United States Patent [19]

Lundbäck

[11] Patent Number: 4,693,714
[45] Date of Patent: Sep. 15, 1987

[54] DOUBLE PUMP ADAPTED FOR USE AS AN ARTIFICIAL HEART

[75] Inventor: Stig Lundbäck, Vaxholm, Sweden

[73] Assignee: Astra-Tech Aktiebolag, Stockholm, Sweden

[21] Appl. No.: 709,555

[22] Filed: Mar. 8, 1985

[30] Foreign Application Priority Data

Mar. 30, 1984 [SE] Sweden .................................. 8401779

[51] Int. Cl.$^4$ ............................................... A61F 2/22
[52] U.S. Cl. .......................................................... 623/3
[58] Field of Search ............................................ 623/3

[56] References Cited

U.S. PATENT DOCUMENTS

| 3,733,616 | 5/1973 | Willis ........................................ 623/3 |
| 4,058,857 | 11/1977 | Runge et al. ............................. 623/3 |
| 4,369,530 | 1/1983 | Robinson et al. ........................ 623/3 |

FOREIGN PATENT DOCUMENTS 1037523  9/1953  France .

*Primary Examiner*—Richard J. Apley
*Assistant Examiner*—James Prizant
*Attorney, Agent, or Firm*—Brumbaugh, Graves, Donohue & Raymond

[57] ABSTRACT

A double pump adapted for use as an artificial heart includes two ventricle-simulating chambers that are provided with respective inlets and outlets having valves incorporated therein and that are separated by a common partitioning wall structure. The wall structure has sections that are driven away from each other to reduce the volumes of respective ventricle chambers and expel liquid from the chambers through the outlets. The wall structure can also move laterally in response to differences in pressure between the chambers and hence change the volumetric ratio between them. This ensures a balanced action between the two halves of the heart-simulating pump during a systole phase and a diastole phase. The link mechanism is actuated by a cord through a motor, although only in one direction in the pressure phase, and hence the aforementioned changed volumes are readjusted primarily through the pressure exerted by the inflowing fluid. The pump may also include a variable volume atrium-simulating chamber communicating with the inlet to each ventricle-simulating chamber and having volume that is controlled in part by an externally acting gas pressure that varies in accordance with changes in the volumes of the ventricle chambers.

6 Claims, 4 Drawing Figures

DOUBLE PUMP ADAPTED FOR USE AS AN ARTIFICIAL HEART

BACKGROUND OF THE INVENTION

Artificial hearts are known and widely used, for example, in heart-lung machines. U.S. Pat. No. 3,097,366 describes and shows a heart pump in which the ventricle-simulating chambers of the pump are worked upon by a common motor driving a plate which causes the chambers to deflate and inflate alternately. The chambers have the form of rubber bags and receive blood from atrium chambers arranged to function as pressure equalizers, i.e., to produce a uniform inflow of blood. The two pumps act on the outflowing blood as "positive" pumps in which the displacement volumes, or stroke volumes, do not vary, and only the rhythm (frequency) can be regulated.

U.S. Pat. No. 3,783,453 describes and shows a double pump in which the ventricle chambers, which have the form of rubber bags, are each enclosed in a respective rigid container and are acted upon externally by a working fluid that is injected into and drawn out of the container. The pump bags are caused to pump alternately, and the function is regulated by a control system in a manner such that the same amount of blood per unit of time, when seen overall, is pumped through the two pumps. This control is effected by separate sensing of the bag volumes.

The present invention is the result of a discovery by the inventor that the human heart does not work in the manner normally presumed. Since this discovery constitutes the background to the invention, it is described briefly below in order to enable the invention to be more readily understood. A more detailed description of the inventor's findings is found in Lundback, S. "Cardiac Pumping and Function of the Ventricular Septum." *Supplementum* 550 1986 *to Acta Physiologica Scandinavica* (ISBN 91-7900-066-5).

It was observed from, inter alia, ultrasonic investigations of the anatomical heart, that during one heart beat the volume of the heart often changes by less than about 10% of its total volume, and that the incoming blood does not pulsate to any great extent while the outgoing blood pulsates strongly. From this it was possible to predict, and to establish clinically, that when the heart beats, the heart musculature, upon contraction of the heart muscles, draws the atrium septum, including the heart valves, down towards the tip of the heart. When the heart muscles then relax, the valve plane is pressed upwards, not by the force exerted by the muscles, but by the intrinsic diastolic pressure of the blood supplied and the force exerted by elastic components within and externally of the heart. Thus, during the systole phase the volume of the ventricle decreases, while that of the atrium increases, wherewith the sum of these volumes decreases slightly and the outer form of the heart thus decreases. Consequently, during the systole period, more blood is pumped out than comes in. The inflow of blood to the atrium continues, however, during the systole period, due to the fact that the atrium volumes increase. During the diastole phase, the valves in the aorta and the pulmonary artery are closed. The inflow of blood to the atrium continues, because the total volume of the heart increases slightly and the valve plane again moves upwards, more or less in response to the amount of blood entering the atrium, whereby the volume of the heart beat in the next following systole phase is determined by the amount of blood supplied during the preceding diastole and systole periods. These discoveries, together with a further discovery pertaining to the regulating function of ventricle septum, must be considered surprising and are thought likely to result in paradigmatic changes in this particular science.

It has also been observed, according to these new discoveries, that the human heart has a particular, natural method of regulating the quantities of blood pumped in the two halves of the heart in a manner to achieve the necessary balance. The regulation is due to the flexibility of the ventricle septum. During the systole phase, in which the volumes of respective heart chambers are compressed, there is experienced on the outlet from the right ventricle to the pulmonary artery a lower counter-pressure, since the resistance to flow in the pulmonary section of the circulatory system is lower than the resistance to flow in the systemic section of the blood circulatory system, which passes through the aorta. The ventricle septum will therefore always take a given position in which it is deflected systolically towards the right chamber. On the other hand, during the diastole phase the ventricle septum is able to adopt a variable position, in dependence upon the pressures prevailing at the two inlets, resulting in a balancing function of the quantities of blood pumped. This balancing function of the heart is of particular importance, and it has been observed, for example, that an infarct concerning the ventricle septum has a worse prognosis than an infarct concerning other parts of the right and left ventricles of the heart. This would seem to be due to the fact that the ventricle septum loses its stablizing function during the systole phase, and becomes rigid and immovable. In consequence, the amount of blood pumped from the right ventricle chamber increases while, at the same time, the output from the left ventricle chamber decreases to the same extent, causing blood to collect in the lungs, resulting in pulmonary edema.

SUMMARY OF THE INVENTION

One object of the invention is to achieve, in a simple fashion, a balanced effect between two pumps in a double pump, so as to enable the pump to be used effectively in a heart-lung machine or as an artificial heart. Another object is to provide a double pump designed for a smooth inflow of fluid, despite a pulsating fluid outflow. Although a certain degree of smoothing is already afforded in practice by known basic designs, since the vascular system nearest the artificial heart, which system can include the remaining upper parts of the atrium, is able to change its volume somewhat, this smoothing effect can be improved by arranging separate atria-simulating volumes, these atria volumes being changed in partial response to changes in the ventricle volumes.

In accordance with a third aspect of the invention, there is provided a double pump which, in addition to accomplishing self-adjustment of the balance between the two blood streams pumped thereby, is also able to self-adjust the absolute values for said pumped blood streams. Such adjustment should not take place under force, with the subsequent risk of tissue damage, but should be effected as a result of "intrinsic pressure." This is achieved by effecting compression of the ventricle-simulating chambers with the aid of a unilateral force, i.e. a force which acts in only one direction. When this force is removed, the chambers can be refilled with the aid of the hydrodynamic pressure and the filling pressure, and during the time interval before the next compulsory compression phase will be filled with precisely the amount of blood required by the body. Suitably, means are provided for detecting when maximum filling is reached, so that when this state is reached the motor can be adjusted in a manner to increase the heart-beat frequency, and to lower said frequency when the blood requirement falls and remains low for an extended period of time.

There is provided, according to the present invention, a double pump adapted for use as an artificial heart comprising two ventricle-simulating chambers arranged side-by-side, each chamber having a fluid inlet and a fluid outlet, and each inlet and outlet having a respective one-way valve mounted therein. A drive assembly periodically and repeatedly reduces the volumes of the chambers to expel fluid from the respective outlets. A common wall structure separates the chambers and includes at least one wall section adapted to move in response to a difference between the respective prevailing pressures in the two chambers and thereby change the respective volumes and equalize the pressures. The respective fluid inlets of the ventricle-simulating chambers may each be connected to a respective atrium-simulating chamber having a fluid inlet, the atrium-simulating chambers being separated by a common partition wall having at least one portion adapted to move in response to a difference between the pressures prevailing in the two atrium-simulating chambers.

In an embodiment of the invention, each chamber (both atria and ventricles) includes a bounding wall portion adapted to move and thereby vary the volume of the chamber, and the pump has a further wall defining with the face of each such movable bounding wall portion externally of the respective chamber a space containing a gas. The spaces associated with the bounding wall portions of the ventricle-simulating chambers communicate with the spaces associated with the bounding wall portions of the atrium-simulating chambers, whereby forces due to changes in gas pressure in the last-mentioned spaces are exerted tending to change the volumes of the atrium-simulating chambers in a direction opposite to the direction of changes in the volumes of the ventricle-simulating chambers.

Other features of the invention include, optionally:

(1) The common wall structure of the ventricle-simulating chambers, the atrium-simulating chambers, or both sets of chambers has two sections adapted to move toward and away from each other correspondingly to increase and decrease the volumes of said chambers. In the case of the ventricle-simulating chambers, the drive applies forces to the two sections to move them away from each other without applying any significant forces to the two sections tending to move them toward each other;

(2) A spring is provided for moving the sections of the common wall structure of the ventricle-simulating chambers toward each other;

(3) The atrium-simulating chambers are located opposite each other on either side of the side-by-side ventricle-simulating chambers.

DESCRIPTION OF THE DRAWINGS

The invention will now be described in more detail with reference to embodiments thereof illustrated in the accompanying drawings, in which.

DESCRIPTION OF THE EMBODIMENTS

Figure 1:
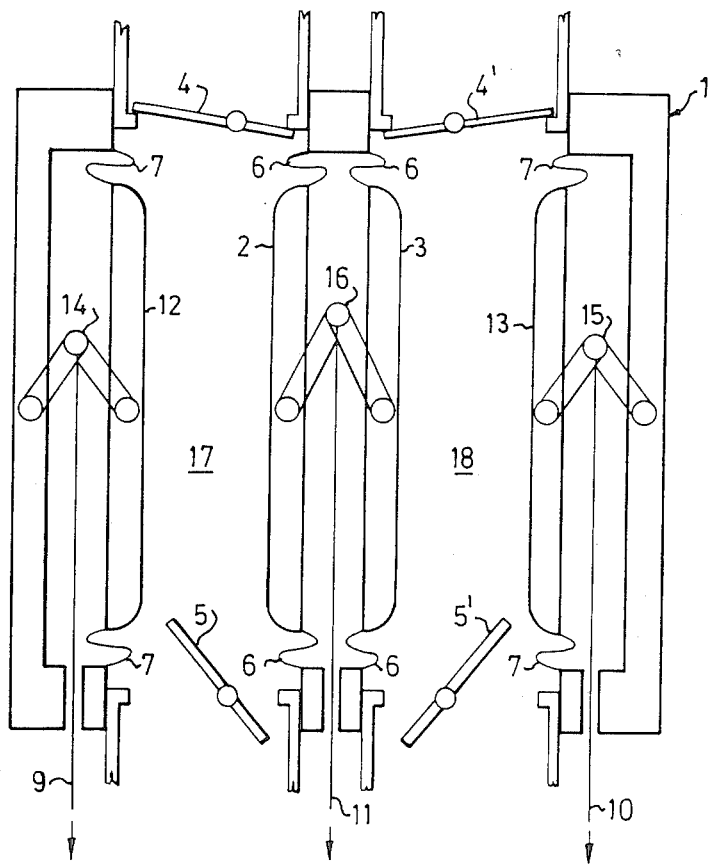
FIG. 1 illustrates a first embodiment of the invention.

In FIG. 1 there is shown a double pump mounted in a rigid outer casing 1. Arranged in the casing is a partitioning wall structure having rigid plate-like sections 2,3, the spacing of which can be increased with the aid of a cord 11 connected to a motor (not shown). The wall structure 2,3 divides the space within the casing 1 into two chambers 17 and 18, each of which is provided with a respective inflow flap valve 5,5' and outflow flap valve 4,4'. When the cord 11 is pulled, the wall sections 2 and 3 are moved apart laterally through the agency of a link system 16 arranged between them and operated by the cord 11. The positions of the wall sections 2, 3 are not permanently fixed, however, since they are suspended from flexible bellows-like members 6 fastened to the casing walls. Consequently, when the cord 11 is pulled, the pressure in the two ventricle chambers 17,18 will initially rise, causing the inflow valves 5 and 5' to close and the outflow valves 4,4' to open when the pressure in the respective chambers exceeds the pressure prevailing externally thereof.

If the externally prevailing pressures are mutually different, one outflow valve will open before the other, and the corresponding chamber will begin to empty before the other, either until the pressure on its output increases or the respective flexible member 6 has been extended to the limit, whereupon continued pulling of the cord 11 will solely influence the volume of the other chamber. When this pulling force is removed, the valves 4,4' will close and the valves 5,5' open, whereupon the chambers take in further fluid, in dependence on the incoming flow of blood. When the double pump is connected to a blood circulatory system, in which one and the same fluid flows in two circuits, the filling mechanism will automatically achieve a balance in the pump displacements effected. For example, should one chamber pump out "too much" blood, this "surplus" blood will be returned to the blood flowing to the other chamber, so as to make compensation. Thus, a balance in volume is achieved without any complicated regulating mechanisms.

The drive motor (not shown) for the double pump may be an electric motor, and a unilateral force, or one-sided force, can be applied, for example, by causing the motor to pull on the cord which acts upon a chamber-defining wall through a system of links or the like. The motor may also take the form of a suitable existing transverse striated autologous muscle activated by an artificially produced electric nerve-signal ("pacemaker"). In certain cases the drive source can be located externally of the body and may be operated pneumatically or hydraulically. When the drive motor is an electric motor, it can be supplied with current through electrodes placed on the skin in accordance with known techniques, or powered by a rechargeable battery implanted in the body, which battery may optionally be recharged through a coil implanted in the body and provided with a rectifying circuit, this circuit being energized through a transformer effect obtained with a primary coil located outside the body and fed with alternating current.

The pump effect can also be supplemented, as in the embodiment of FIG. 1, by providing each of the ventricle-simulating chambers with an additional laterally movable wall 12,13, actuated by cords 9,10 via link systems 14,15. Walls 12,13 are arranged with flexible members 7 attached to the casing 1. These cords can be replaced with gas-operated devices, for example devices operated from a compressed-air source. The same also applies to the cord 11, even though unilaterally acting forces are required with the view of enabling self-adjustment of the total amounts of fluid pumped, in accordance with what was said in the introduction.

The embodiment of FIG. 1 can also be modified by omitting the two movable wall sections 2,3 and the associated drive wire 11 and links 16 and substituting a common wall structure having a single wall section that is movable in response to a pressure difference between the chambers 17 and 18 and thereby changes the respective volumes of the chambers and equalizes the pressures. In this case the pumping is done by the powered drive means constituted by the respective movable walls 12 and 13, link systems 14 and 15, cords 9 and 10 and motor (not shown) or by pneumatic means.

The cord 11 is single-acting (as are the cords 9 and 10) and will, therefore, only effect contraction of the ventricle-simulating chambers. The passage of blood into the chambers during the diastole phase takes place due to the diastolic blood pressure independently of a force from the drive cord. It may be desirable to control the filling process by applying a force causing the movable wall-sections to move in directions that result in increasing the volumes of the chambers, against the action of a controlled or preset counter-pressure. For example, if the space between the wall sections 2 and 3 (and behind the sections 12 and 13) is set to a given pressure value, such as by connecting that space to a reservoir chamber (not shown), refilling of the chambers will take place against the action of this pressure and will cease when the inflow pressure is too low to force the wall sections 2,3 together, or to move the aforesaid additional side wall sections 12 and 13 outwardly.

Figure 2A:
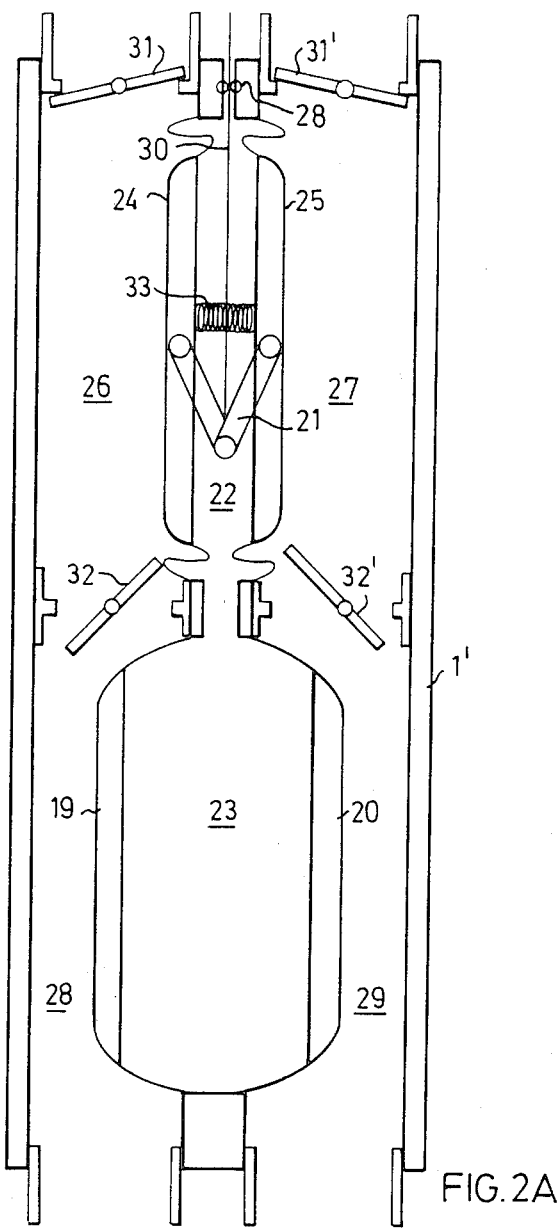
FIGS. 2A and 2B, illustrate a second embodiment, in two different positions.
Figure 2B:
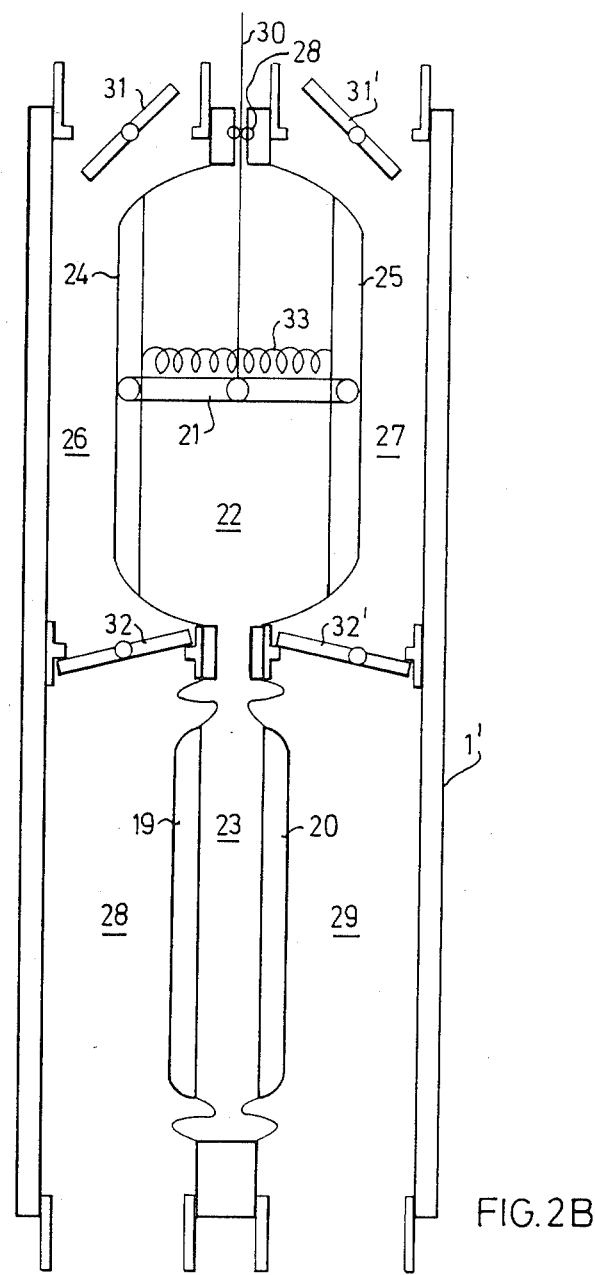

FIGS. 2A and 2B illustrate an embodiment of an artificial heart designed in accordance with the invention, and show the positions of the simulated-heart components at the end of a diastole phase and at the end of a systole phase, respectively. This embodiment comprises an inflexible casing 1' in which there is arranged a partition that divides the casing into two parts. The partition comprises two wall structures, each of which comprises a pair of wall sections which form inter-communicating, gas (air) filled spaces 22 and 23. The wall sections 24, 25 of one wall structure can be moved apart by means of a link system 21 and a cord-like actuator 30 (unilateral force). Arranged between the two wall structures are flap valves 32 and 32', while flap valves 31, 31' are arranged adjacent opposite portions of the separatable wall sections 24, 25. The wall sections are inflexible at their central regions and flexible at their edge regions, which may have the form of bellows. The valves 32, 32' define on one side the ventricle volumes 26 and 27, which form a pump, and on the other side the atrium volumes 28 and 29. By pulling on the cord 30, which passes out of the casing 1' through an opening provided with sealing means 28, the wall sections 24 and 25 are moved apart, as illustrated in FIG. 2B, thereby pumping blood from the chambers 26 and 27 through the valves 31, 31'. Meanwhile, the total volume of the spaces 22 and 23 between the respective walls 24, 25 and 19, 20 increases, so the gas pressure in those spaces falls. The fall in gas pressure in the space 23 facilitates the flow of blood into the atrium chambers 28, 29 during the systolic phase, and the wall sections 19, 20 move toward each other as the chambers 28, 29 are filled. When the incoming flows into the chambers 28 and 29 are different, the walls 19 and 20 will move toward each other at different speeds. The elasticity of the air in the spaces 22,23 will cause the flow of blood into the chambers 28 and 29 to be dampened, which in turn maintains a uniform inflow rate.

Because the wall sections 24,25 of the partition between the two ventricle chambers 26, 27 can move laterally, either both in one direction or each in a different direction during the systole phase, when the valves 32 and 32' are closed, the blood will primarily be forced out through the outlet at which the lowest pressure prevails, until the bellows on one side have been extended to their maximum extent, after which the remainder of the displacement volume is expelled through the outlet where the higher pressure prevails.

In the diastole phase (FIG. 2A) the wall-sections 24 and 25 are moved toward each other under the action of a weak spring 33. The spring 33 enhances the transfer of blood from the atrium chambers 28 29 through the valves 32,32' by collapsing the space 22 and enlarging the space 23 due to movement of air from the space 22 to the space 23. Like the walls 19 and 20, the walls 24 and 25 will approach one another at different speeds, if the fluid flows through the valves 32 and 32' differ, which can result in volumes 26 and 27, and therewith displacement volumes in the next-following systole phase, being of different sizes. In this way it is insured that inflows of differing pressures will be rapidly balanced out.

Figure 3:
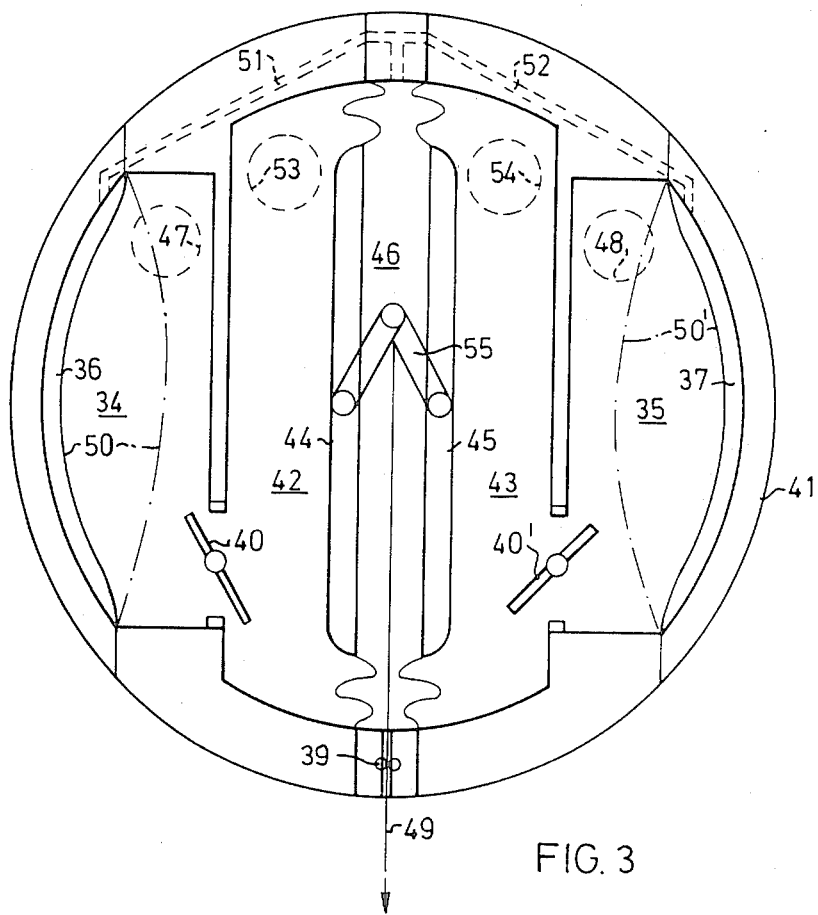
FIG. 3 illustrates a compact version of a double pump.

Another embodiment is illustrated schematically and in cross-section in FIG. 3, this embodiment exhibiting similarities to an anatomical heart. The ventricle chambers 42 and 43 are separated one from the other by a double wall structure comprising two laterally movable, rigid wall sections 44 and 45, which are arranged to be moved apart by means of a cord 49 connected to a link arrangement 55 and penetrating the casing 41 through an opening provided with sealing means 39. The wall sections are supported by bellows-like structures located around their perimeters and fastened to the casing 41. The chambers 42 and 43 communicate with atrium chambers 34 and 35, respectively, through flap valves 40 and 40'. Although not shown in the Figure, outflow valves are mounted in the outflow tubes leading from the casing 41 at openings 53 and 54. Inflow tubes lead to casing 41 at openings 47 and 48 in the respective chambers 34 and 35, respectively.

For the purpose of achieving the desired pumping effect, the atrium-simulating chambers 34 and 35 are defined in part by peripheral movable walls 50 and 50' respectively, which may be movable by virtue of being flexible. These walls are movable between an outer extreme position, shown in full lines, and an inner extreme position, shown in broken lines, thereby enabling variation in the volumes of the chambers 34 and 35. The walls 50, 50' also define with the casing, to which they are secured, air-filled spaces 36, 37 which communicate with the space 46 located between the wall sections 44, 45, via passages 51 and 52., This arrangement functions in substantially the same manner as the embodiment according to FIGS. 2A and 2B, but can be made much more compact.

The inlets and outlets 47, 48 and 53, 54 have been shown in broken lines, and can be located at either end of the casing, as seen from the cross-sectional plane of the paper. Preferably, however, the inlets and outlets lie on opposite sides of the plane of the paper, since in this way the flow pattern is less liable to cause fluid to become stationary, which could lead to coagulation of the blood. The embodiment illustrated in FIG. 3 is able to function fully as a two-chamber heart.

The air-filled space 46 between the wall sections 44, 45 and the spaces 36 and 37 located externally of respective pliable walls 50, 50' serve as auxiliary volumes which establish at the inlets 47, 48 a minimum pressure at which blood is able to enter. This auxiliary volume can be arranged to communicate with a further volume, via pressure-restricting valves, such as with an air-bag surrounding the pump and accomodating the motor. Such a bag can also serve to impart to the arrangement as a whole, a density corresponding to the mean density of the thorax content, thereby enabling the arrangement to "move" in its place and to be independent of the position adopted by the patent.

Filling of the chambers can, advantageously, be assisted by placing a relatively weak spring (not shown but see FIGS. 2A and 2B) between the wall sections 44, 45. Alternatively, the walls 50 and 50' can be made elastic. This elastic effect, which affords filling of the ventricle-simulating chambers and emptying the atrium chambers, complements the effect produced by the elasticity of the gas in the gas-filled chambers, while these two effects amplify the damping effect of the atrium on the inflowing blood, these input fluid flows being smoothed despite the pronounced pulsations of the outflows.

I claim:

1. A double pump adapted for use as an artificial heart comprising a housing, two ventricle-simulating chambers arranged side-by-side in the housing, each chamber having a fluid inlet and a fluid outlet, and each inlet and outlet having a respective one-way valve mounted therein, a common partition wall structure separating the chambers and partly defining them and having two spaced-apart wall sections, means mounting said wall sections in the housing for movement relative to the housing in response to a difference between the respective prevailing pressures in the two chambers and for thereby changing the respective volumes and equalizing the pressures, and powered drive means for moving said wall sections away from each other intermittently and repeatedly to reduce the volumes of the chambers to expel fluid from the respective outlets.

2. A double pump according to claim 1 wherein the housing and wall sections define a variable volume space adapted to contain a gas, and further comprising two atrium-simulating chambers, each in fluid communication with the inlet of a respective ventricle-simulating chamber and having an inlet, each atriumsimulating chamber having a bonding wall portion adapted to move and thereby vary the volume thereof, wall mcans defining with said bonding wall portion of each atrium-simulating chamber a variable volume space adapted to contain a gas, and means communicating the spaces associated with the atrium-simulating chambers with the space associated with the wall sections of the ventricle-simulating chambers, whereby movements of the wall sections toward and away from each other vary the gas pressures in said spaces and tend to change the volumes of the atrium-simulating chambers in directions opposite to changes in volumes of the ventricle-simulating chambers.

3. A double pump according to claim 2, wherein the atrium-simulating chambers are located opposite each other on either side of the side-by-side ventricle-simulating chambers.

4. A double pump according to claim 2 wherein the atrium-simulating chambers are located side-by-side, the bounding wall portions thereof are located adjacent each other in spaced-apart relation, and the variable volume spaces associated with the atrium-simulating chambers are defined by a common space between said wall portions.

5. A double pump according to claim 2 wherein each wall section includes a substantially rigid part and the powered drive means includes mechanical means coupled to the respective rigid parts for applying forces to the two wall sections to move them away from each other without applying any substantial forces to them tending to move them toward each other.

6. A double pump according to claim 5, and further comprising spring means for moving the sections of the common wall structure of the ventricle-simulating chambers toward each other.

* * * * *